(12) United States Patent
Swan

(10) Patent No.: US 6,278,018 B1
(45) Date of Patent: Aug. 21, 2001

(54) SURFACE COATING AGENTS

(75) Inventor: Dale G. Swan, St. Louis Park, MN (US)

(73) Assignee: SurModics, Inc., Eden Prairie, MN (US)

( * ) Notice: Subject to any disclaimer, the term of this patent is extended or adjusted under 35 U.S.C. 154(b) by 0 days.

(21) Appl. No.: 09/460,551

(22) Filed: Dec. 14, 1999

(51) Int. Cl.⁷ .................. C07C 309/28; C07C 309/37
(52) U.S. Cl. .................................................. 562/53
(58) Field of Search .................................. 562/53

(56) References Cited

U.S. PATENT DOCUMENTS

| | | | |
|---|---|---|---|
| 4,001,202 | * 1/1977 | Dilling et al. . | |
| 4,118,382 | * 10/1978 | Jager et al. . | |
| 4,309,453 | 1/1982 | Reiner et al. | 427/54 |
| 4,722,906 | 2/1988 | Guire | 436/501 |
| 4,973,493 | 11/1990 | Guire | 427/2 |
| 4,979,959 | 12/1990 | Guire | 623/66 |
| 4,999,186 | * 3/1991 | Sabatelli et al. . | |
| 5,002,582 | 3/1991 | Guire et al. | 623/66 |
| 5,414,075 | 5/1995 | Swan et al. | 568/333 |
| 5,512,329 | 4/1996 | Guire et al. | 427/508 |
| 5,714,360 | 2/1998 | Swan et al. | 435/174 |
| 5,858,653 | * 1/1999 | Duran et al. . | |

* cited by examiner

Primary Examiner—Johann Richter
Assistant Examiner—Sikarl A. Witherspoon
(74) Attorney, Agent, or Firm—Fredrikson & Byron, P.A.

(57) ABSTRACT

Compounds useful as surface coating agents, including compounds of the formula:

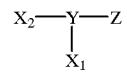

wherein $X_1$ comprises a first photoreactive species; $X_2$ comprises a second photoreactive species; Y comprises a nonpolymeric core molecule comprising an aromatic group; and Z comprises at least one charged group. The Y core can include an aromatic group such as a benzene radical, the charged groups Z can be independently selected from the organic acids that include sulfonic acid, carboxylic acid, and phosphoric acid, and the photoreactive species of $X_1$ and $X_2$ can independently be aryl ketones, such as those selected from the group acetophenone, benzophenonie, anthraquinone, anthrone, and anthrone-like heterocycles, and their substituted derivatives. Examples of such coating agents include 4,5-bis(4-benzoylphenylmethyleneoxy)benzene-1,3-disulfonic acid di(potassium and/or sodium) salt, 2,5-bis(4-benzoylphenylmethyleneoxy)benzene-1,4-disulfonic acid di(potassium and/or sodium) salt (Compound II), and 2,5-bis(4-benzoylphenylmethyleneoxy)benzene-1-sulfonic acid monopotassium and/or monosodium salt.

1 Claim, No Drawings

SURFACE COATING AGENTS

TECHNICAL FIELD

The present invention relates to chemical compounds providing both charged groups as well as photoreactive species. In a related aspect, the invention relates to chemical compounds for use as surface coating agents.

BACKGROUND OF THE INVENTION

The chemical modification of surfaces to achieve desired chemical and/or physical characteristics has been previously described. For example, U.S. Pat. Nos. 4,722,906; 4,973,493; 4,979,959; 5,002,582; and 5,512,329 (each of which is commonly owned by the assignee of the invention described herein, and the disclosure of each is incorporated herein by reference), relate to surface modification by the use of latent reactive groups to achieve covalent coupling of reagents such as biomolecules and synthetic polymers to various substrates. The preferred latent reactive group is typically described as a photochemically reactive functional group ("photoreactive species"). When exposed to an appropriate energy source, a photoreactive species undergoes a transformation from an inactive state (i.e., ground state) to a reactive intermediate capable of forming covalent bonds with appropriate materials.

Such latent reactive groups can be used, for instance, to first derivatize a target molecule (e.g., thermochemically), in order to then photochemically attach the derivatized target molecule to a surface. Such a sequential approach is suitable in many situations, but can lack such attributes as speed, versatility, and ease of use, particularly when used with target molecules that are inherently difficult to first derivatize or under conditions that would result in loss of biological activity.

Latent reactive groups can also be used to prepare photoactivatable heterobifunctional molecules as linking agents, e.g., having a photoreactive species at one end or portion with a thermochemically attachment group at another (see, e.g., the above-captioned '582 patent, and U.S. Pat. No. 4,309,453, Reiner et al.). Such linking agents can be used to either attach nonreactive compounds to a surface or to prime a relatively inert surface in order to render it reactive upon exposure to suitable actinic radiation.

U.S. Pat. No. 5,414,075 (commonly owned by the assignee of the present invention and incorporated by reference herein), describes the use of linking agents to prime a surface to provide the surface with photoactivatable groups. This patent describes a restrained, multifunctional reagent useful for priming a support surface, or for simultaneous application with a target molecule to a support. Reagents such as those described above, including those described in the '075 patent, are generally hydrophobic. As a result, they are of relatively low solubility in aqueous systems, thereby often limiting their usefulness in hydrophilic applications.

U.S. Pat. No. 5,714,360, also commonly owned by the present assignee (and also incorporated herein by reference), describes a chemical linking agent comprising a di-or higher functional photoactivatable charged compound. The linking agent provides at least one group that is charged under the conditions of use, in order to provide improved water solubility, and two or more photoactivatable groups in order to allow the agent to be used as a linking agent in aqueous systems. The "Y group" that provides the core radical is defined as a radical containing one or more charged groups, such as the linear and heterocyclic nitrogen-containing (e.g., quaternary ammonium) radicals exemplified therein. In a preferred embodiment, the charged groups include, but are not limited to, salts of organic acids (such as sulfonate, phosphonate, and carboxylate groups), onium compounds (such as quaternary ammonium, sulfonium, and phosphonium groups), and protonated amines, as well as combinations thereof. The photoreactive species can be provided by two or more radicals of an aryl ketone such as benzophenone.

While the reagents of the art are sufficient, if not preferred, for many applications, there remain applications in which various other properties or attributes, such as water solubility, ease of synthesis and/or hemocompatability, are not optimally provided by the reagents of the art.

SUMMARY OF THE INVENTION

The present invention provides compounds useful as coating agents. In one aspect, the present invention provides a compound comprising a nonpolymeric core molecule comprising an aromatic group, the core molecule having attached thereto, either directly or indirectly, one or more substituents comprising negatively charged groups, and two or more photoreactive species, wherein the photoreactive species are provided as independent photoreactive groups. The first and second photoreactive species of the present coating agent can, independently, be identical or different.

In a preferred embodiment the reagent comprises a compound of the formula:

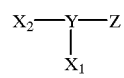

wherein $X_1$ comprises a first photoreactive species;
$X_2$ comprises a second photoreactive species;
Y comprises a nonpolymeric core molecule comprising an aromatic group; and
Z comprises at least one charged group.

In such an embodiment, for instance, Y can include an aromatic group such as a benzene radical, the charged groups Z can be independently selected from the salts of organic acids that include sulfonic acid, carboxylic acid, and phosphoric acid, and the photoreactive species of $X_1$ and $X_2$ can independently be aryl ketones, such as those selected from the group acetophenone, benzophenone, anthraquinone, anthrone, and anthrone-like heterocycles, and their substituted derivatives.

A coating agent of the invention has broad applicability, particularly since it can be used in surface modification reaction systems where previous agents have not been effective or optimal. In particular, the presence of one or more charged groups (e.g., salts of sulfonic, carboxylic and phosphoric acids) provides the agent with enhanced water solubility. This, in turn, allows the coating agent to be used in reaction systems favoring water soluble agents. A coating agent of the present invention thereby provides an improved combination of such properties as coating density and structural stability, allowing the agent to be used in a broad range of reaction systems.

Moreover, the presence of photoreactive species permits the agent to be used with a wide variety of support surfaces. The coating agent can be used alone as a coating composition for a support surface, in order to provide a surface primed with the coating agent itself. In this embodiment, the coating agent provides the surface with desirable properties of the coating agent itself, such as, for example, antithrombogenicity, lubricity, hemocomopatability, wettability/hydrophilicity, durability of attachment to the surface, biocompatability, and bacterial adhesion.

DETAILED DESCRIPTION

Compounds of this invention comprise a nonpolymeric core molecule comprising an aromatic group, the core molecule having attached thereto, either directly or indirectly, one or more substituents comprising negatively charged groups, and two or more substituents comprising photoreactive species, wherein the photoreactive species are provided as independent photoreactive groups.

In a preferred embodiment, the core is provided as the residue of a polyhydroxy benzene starting material (e.g., formed as a derivative of hydroquinone, catechol, or resorcinol), in which the hydroxy groups have been reacted to form an ether (or ether carbonyl) linkage to a corresponding plurality of photogroups.

In one embodiment, a coating agent of this invention further comprises one or more optional spacers that serve to attach a core molecule to corresponding photoreactive species, the spacer being selected from radicals with the general formula:

—O—$(CH_2)_n$—, and

—$(C_2H_4O)_m$—$C_2H_4O$—, wherein n is a number greater or equal to 1 and less than about 5, and m is a number greater or equal to 1 and less than about 4.

In a particularly preferred embodiment, such coating agents are selected from the group 4,5-bis(4-benzoylphenylmethyleneoxy)benzene-1,3-disulfonic acid di(potassium and/or sodium) salt, 2,5-bis(4-beizoylphenylmethyleneoxy)benzene-1,4-disulfonic acid di(potassium and/or sodium) salt, 2,5-bis(4-benzoylphenylmethyleneoxy)benzene-1-sulfonic acid monopotassium and/or monosodium salt.

| Agent | Formula |
|---|---|
| 4,5-bis(4-benzoyl-phenylmethyleneoxy)benzene-1,3-disulfonic acid di(potassium and/or sodium) salt<br>Compound I | 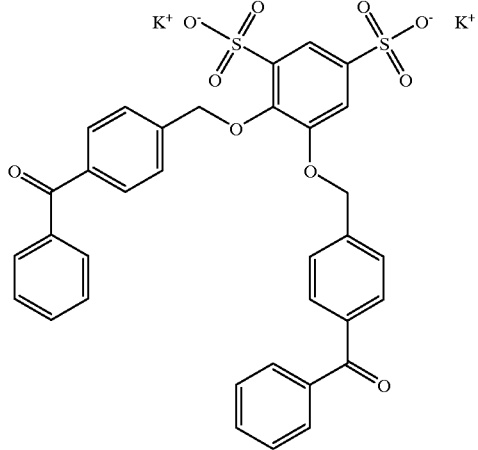 |
| 2,5-bis(4-benzoyl-phenylmethyleneoxy)benzene-1,4-disulfonic acid di(potassium and/or sodium) salt<br>Compound II | 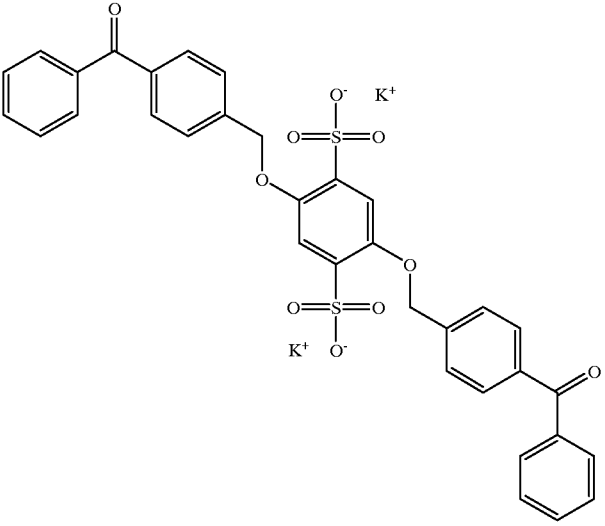 |

-continued

| Agent | Formula |
|---|---|
| 2,5-bis(4-benzoyl methyleneoxy)benzene-1-sulfonic acid monopotassium and/or monosodium salt Compound III | 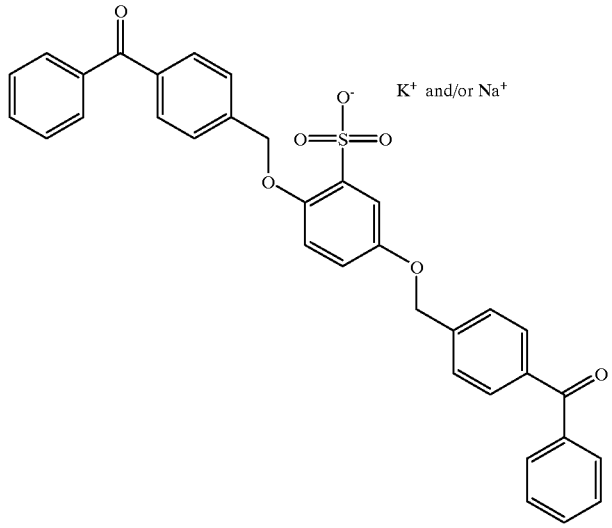 K⁺ and/or Na⁺ |

Suitable core molecules of the present invention include nonpolymeric radicals having a low molecular weight (e.g., 100–1000 MW). Suitable core molecules provide an improved combination of such properties as coating density, structural stability, ease of manufacture, and cost. Further, core molecules can be provided with water soluble regions, biodegradable regions, hydrophobic regions, as well as polymerizable regions. Examples of suitable core molecules include cyclic hydrocarbons, such as benzene and derivatives thereof.

As used herein, a "charged" group generally refers to a group that is present in ionic form in solution, i.e., carries an electrical charge under the conditions (e.g., pH) of use. The charged groups are present, in part, to provide the compound with desired water solubility. Additionally, such charged groups provide a combination of such desirable characteristics as antithrombogenicity and hemocompatability.

The type and number of charged groups in a preferred coating agent are sufficient to provide the agent with a water solubility (at room temperature and optimal pH) of at least about 0.1 mg/ml, and preferably at least about 0.5 mg/ml, and more preferably at least about 1 mg/ml. Given the nature of the surface coating process, coating agent solubility levels of at least about 0.1 mg/ml are generally adequate for providing useful coatings of target molecules (e.g., polymer layers) on surfaces.

The coating agent of the present application can thus be contrasted with many coating 5 agents in the art, which are typically considered to be insoluble in water (e.g., having a comparable water solubility in the range of about 0.1 mg/ml or less, and more often about 0.01 mg/ml or less). For this reason, conventional coating agents are typically provided and used in solvent systems in which water is either absent or is provided as a minor (e.g., less than about 50% by volume) component.

Examples of suitable charged groups include salts of organic acids (e.g., sulfonate, phosphonate, and carboxylate groups), as well as combinations thereof. A preferred charged group for use in preparing coating agents of the present invention is a sulfonic acid salt, e.g., derivatives of $SO_3^-$ in which the counterion is provided by the salts of Group I alkaline metals (Na, K, Li ions) to provide a suitable positively charged species.

Photoreactive species are defined herein, and preferred species are sufficiently stable to be stored under conditions in which they retain such properties. See, e.g., U.S. Pat. No. 5,002,582, the disclosure of which is incorporated herein by reference. Latent reactive groups can be chosen that are responsive to various portions of the electromagnetic spectrum, with those responsive to ultraviolet and visible portions of the spectrum (referred to herein as "photoreactive") being particularly preferred.

Photoreactive species respond to specific applied external stimuli to undergo active specie generation with resultant covalent bonding to an adjacent chemical structure, e.g., as provided by the same or a different molecule. Photoreactive species are those groups of atoms in a molecule that retain their covalent bonds unchanged under conditions of storage but that, upon activation by an external energy source, form covalent bonds with other molecules.

The photoreactive species generate active species such as free radicals and particularly nitrenes, carbenes, and excited states of ketones upon absorption of electromagnetic energy. Photoreactive species can be chosen to be responsive to various portions of the electromagnetic spectrum, and photoreactive species that are responsive to e.g., ultraviolet and visible portions of the spectrum, arc preferred and can be referred to herein occasionally as "photochemical group" or "photogroup."

The use of photoreactive species in the form of photoreactive aryl ketones are preferred, Such as acetophenone, benzophenone, anthraquinone, anthlone, and anthrone-like heterocycles (i.e., heterocyclic analogs of anthrone such as those having N, O, or S in the 10-position), or their substituted (e.g., ring substituted) derivatives. Examples of preferred aryl ketones include heterocyclic derivatives of anthrone, including acridone, xanthone, and thioxanthone, and their ring substituted derivatives. Particularly preferred are thioxanthone, and its derivatives, having excitation energies greater than about 360 nm.

The functional groups of such ketones are preferred since they are readily capable of undergoing the activation/inactivation/reactivation cycle described herein. Benzophenone is a particularly preferred photoreactive moiety, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source. Photoactivatible aryl ketones such as betizophenone and acetophenone are of particular importance inasmuch as these groups are subject to multiple reactivation in water and hence provide increased coating efficiency.

The azides constitute a preferred class of photoreactive species and include derivatives based on arylazides ($C_6R_5N_3$) such as phenyl azide and particularly 4-fluoro-3-nitrophenyl azide, acyl azides (—CO—$N_3$) such as benzoyl azide and p-methylbenzoyl azide, azido formates (—O—CO—$N_3$) such as ethyl azidofoiiate, phenyl azidoformate, sulfonyl azides (—$SO_2$—$N_3$) such as benzenesulfonyl azide, and phosphoryl azides (RO)$_2$PON$_3$ such as diphenyl phosphoryl azide and diethyl phosphoryl azide. Diazo compounds constitute another class of photoreactive species and include derivatives of diazoalkanes (—CHN$_2$) such as diazomethane and diphenyldiazomethane, diazoketones (—CO—CHN$_2$) such as diazoacetophenone and 1-trifluoromethyl-1-diazo-2-pentanone, diazoacetates (—O—CO—CHN,) such as t-butyl diazoacetate and phenyl diazoacetate, and beta-keto-alpha-diazoacetates (—CO—CN$_2$—CO—O—) such as t-butyl alpha diazoacetoacetate. Other photoreactive species include the diazirines (—CHN$_2$) such as 3-trifluoromethyl-3-phenyldiazirine, and ketenes (—CH=C=O) such as ketene and diphenylketene.

Upon activation of the photoreactive species, the coating agents are covalently bound to each other and/or to the material surface by covalent bonds through residues of the photoreactive species. Exemplary photoreactive species, and their residues upon activation, are shown as follows (wherein R and R' can be the same or different independently represent any non-interfering group).

| Photoreactive | Group | Residue Functionality |
|---|---|---|
| aryl azides | amine | R-NH-R' |
| acyl azides | amide | R-CO-NH-R' |
| azidoformates | carbamate | R-O-CO-NH-R' |
| sulfonyl azides | sulfonamide | R-SO$_2$-NH-R' |
| phosphoryl azides | phosphoramide | (RO)$_2$PO-NH-R' |
| diazoalkanes | new C-C bond | |
| diazoketones | new C-C bond and ketone | |
| diazoacetates | new C-C bond and ester | |
| beta-keto-alpha-diazo-acetates | new C-C bond and beta-ketoester | |
| aliphatic azo | new C-C bond | |
| diazirines | new C-C bond | |
| ketenes | new C-C bond | |
| photoactivated ketones | new C-C bond and alcohol | |

In one embodiment, the coating agent of the present invention further includes optional spacers between the nonpolymeric aromatic core molecule and one or more of the photoreactive species. A spacer is provided in situations when it is desired to provide more distance between the photoreactive species and the core molecule. For example, it can be desirable to provide a spacer to avoid steric hindrance that may result between the core molecule and the photoreactive species, thus inhibiting the photoreactive species from forming covalent bonds with a support surface (in terms of the second photoreactive species), or from serving as a linking agent for attaching natural and synthetic polymers to a surface.

The coating agent can be applied to the surface of interest in any suitable manner. For example, the coating agent can be applied by dip coating or by dispersing the agent on the surface (for example, by spray coating). Suitable methods of application include application in solution, dipping, spray coating, knife coating, and roller coating. In a particularly preferred embodiment, the coating agent is applied to the surface via spray coating, as this application method provides increased density of the coating agent on the support surface, thereby improving durability.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

EXAMPLES

Example 1

Preparation of 4,5-bis(4-benzoylphenylmethyleneoxy)benzene-1,3-disulfonic Acid disodium Salt (Compound I)

4,5-bis(4-benzoylphenylmethyleneoxy)benzene-1,3-disulfonic acid disodium salt (Compound I) was prepared as follows. An amount (9.0 g, 0.027 moles) of 4,5-dihydroxy 1,3-benzene disulfonic acid disodium salt monohydrate was added to a 250 ml, 3 necked round bottom flask fitted with an overhead stirrer, gas inlet port, and reflux condenser. An amount (15 g, 0.054 moles) of 4-bromomethylbenzophenonie (BMBP), 54 ml tetrahydrofuran (THF), and 42 ml deionized water were then added. The flask was heated with stirring under an argon atmosphere to reflux. The argon atmosphere was maintained during the entire time of refluxing.

After reflux was reached, 9.0 ml (6 N, 0.054 moles) of a sodium hydroxide solution was added through the reflux condenser. The reaction was stirred under reflux for 3 hours. After this time, a second portion of BMBP, 3.76 g (0.014 moles), and 3.6 ml (6 N, 0.022 moles) of sodium hydroxide were added. The reaction was continued under reflux for more than 12 hours, after the second BMBP addition.

The reaction mixture was evaporated at 40° C. under vacuum on a rotary evaporator to give 46 g of a yellow paste. The paste was extracted by suspending three times in 50 ml of chloroform n at 40° C. for 30 minutes. A centrifuge was used to aid in the decanting of the chloroform from the solid. The solid was collected on a Buchner funnel, after the last extraction, and air dried for 30 minutes. The solid was then dried by using a rotary evaporator with a bath temperature of 50° C. at a pressure of about 1 mm for 30 minutes.

The dried solid, 26.8 g, was recrystallized from 67 ml of water and 67 ml of methanol. The dried purified product amounted to 10.4 g (the theoretical yield was 19.0 g) with absorbance of 1.62 at 265 nm for a concentration of 0.036 mg/ml.

Example 2

Preparation of 2,5-bis(4-benzoylphenylmethyleneoxy)benzene-1,4-disulfonic Acid dipotassium Salt (Compound II)

2,5-bis(4-benzoylphenylmethyleneoxy)benzene-1,4-distilfonic acid disodium salt (Compound II) was prepared as follows. An amount (15.0 g, 0.043 moles) of 2,5-dihydroxy 1,4-benzene disulfonic acid dipotassium salt was added to a 500 ml, 3 necked round bottom flask fitted with an overhead stirrer, gas inlet port, and reflux condenser. An amount (23.75 g , 0.086 moles) of BMBP, 10.0 g (0.094 moles) of sodium carbonate, 90 ml of methanol, and 90 ml deionized water were then added. The flask was heated with stirring under an argon atmosphere to reflux. The argon atmosphere was maintained during the entire time of refluxing. The reaction was stirred under reflux for 2 hours.

A second portion of BMBP, 6.25 g (0.023 moles), and 2.65 g (0.025 moles) sodium carbonate were added. The reaction was continued under reflux for 2 more hours, after the second BMBP addition.

The reaction mixture was filtered and dried to give 43.6 g of a semi-dry solid. The solid was dried to give 26.8 g of a gray powder (the theoretical yield was 31 g).

Example 3

Preparation of 2,5-bis(4-benizoylphenylmethyleneoxy)benzenesulfoniic Acid sodium and/or potassium Salt (Compound III)

2,5-bis(4-benzoylplhenylmethyleneoxy)benzenesulfonic acid monosodium and/or monopotassium salt was prepared as follows. An amount (1.98 g , 0.0087 moles) of 2,5-dihydroxybenzene sulfonic acid potassium salt was added to a 100 ml, 3 necked round bottom flask fitted with an overhead stirrer, gas inlet port, and reflux condenser. An amount (4.75 g, 0.017 moles) of BMBP; 2.9 ml (0.017 moles) of 6N sodium hydroxide; 18 ml of methanol; and 14 ml of deionized water were then added. The flask was heated with stirring under an argon atmosphere to reflux. The argon atmosphere was maintained during the entire time of refluxing. The reaction was stirred under reflux for 1 hour.

A second portion of BMBP, 1.25 g (0.0045 moles), and 1.1 ml (0.0066 moles) of 6N sodium hydroxide were added. The reaction was continued under reflux for 1 more hour, after the second BMBP addition.

At the end of the reaction there were two liquid layers present. The reaction mixture had solidified 2 days later; the solid was filtered and dried to give 5.95 g of a light tan solid (the theoretical yield was 5.1 to 5.3 g).

Example 4

Compound I Coating on Hydrogel Matrix

An experiment was performed to demonstrate the effectiveness of using Compound I as a coating agent on a polyvinylpyrrolidone (PVP) based, lubricious, hydrogel matrix.

The concentrations for the formulations came out of design of experiments performed with Compound I/$PVP_{k90}$ combinations. Three factors were varied for each experiment, $PVP_{k90}$ concentration (20–40 mg/ml), Compound I concentration (0.3–0.7 mg/mil), and % isopropyl alcohol (10–40% by volume IPA). From the experiments it was determined that high $PVP_{k90}$ level (40 mg/ml), high Compound I (0.7 mg/ml), and low % IPA level (10%) was the most favorable formulation for the Compound I/$PVP_{k90}$ combinations.

A solution of Compound I and PVP was prepared and applied to the surface of a polyvinylchloride (PVC) intermittent urinary catheter. This solution contained 0.7 mg/ml of Compound I and 40 mg/ml of $PVP_{k90}$ in a solvent system of 10% (by volume) isopropyl alcohol and 90% (by volume) water.

The surface of the PVC catheter was cleaned by wiping with an alcohol soaked cloth. The coating was applied to the catheter by a dip method at a speed of 1 cm/s. The coating was illuminated wet to dry with a Dymax lamp (as previously described) for 4 minutes, while the catheter was rotated.

Durability and Lubricity

To assess lubricity and tenacity of coated parts, frictional force over both the first and last 5 cycles of a 60 cycle test was evaluated. The coated catheters were evaluated by a horizontal sled style friction test method (modified ASTM D-1894, as described below).

Regenerated cellulose (Spectra/Por molecular porous membrane, MWCO: 6–8,000, flat width 50 mm, part #132665, available from Spectrum Medical Industries, Inc., Los Angeles, Calif.) was hydrated and then wrapped around a 200 gram stainless steel sled. The sheet of cellulose was clipped together tightly on the opposite side of the sled. The sled with rotatable arm was then attached to a 250 gram Chatillon Digital Force Gauge (DGGHS, 250×0.1) with computer interface. The testing surface was mounted on a 22.5 inch positioning rail table with micro-stepper motor control (Compumotor SX6 Indexer/Drive).

The parts to be tested were hydrated in deionized water and clamped onto the test surface 1 inch (or approximately 2.5 cm) apart. The hydrated cellulose covered sled was placed on top of the parts. Initial force measurements were taken while the sled moved at 0.5 cm/sec over a 5 cm section for five push/pull cycles. The sled then continued cycling over the coated samples 50 push/pull cycles at 5 cm/sec to simulate abrasion. The velocity was then decreased back to 0.5 cm/sec and the final force measurements were taken over another five push/pull cycles.

As shown in FIG. 1 below, the results show that the Compound I/$PVP_{k90}$ combination provided a superior lubricious hydrogel matrix in terms of durability. For the Compound I formulation, the grams of force remained relatively constant for all 60 cycles, indicating a durable coating.

FIG. 1 Horizontal Sled Style Friction Test
200g Stainless Steel Sled Covered
in Regenerated Cellulose

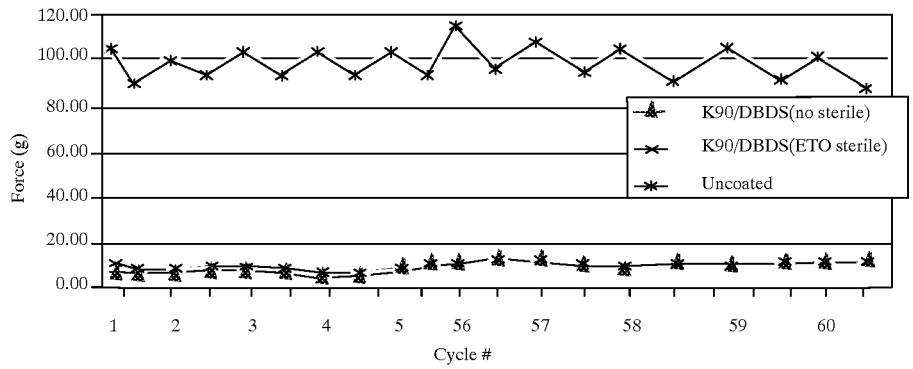

Example 5

Partial Thromboplastin Time of Coating Agents

An experiment was conducted to determine the hemocompatability of the coating agent when attached to a support surface.

A useful test in determining the hemocompatibility of a reagent is the partial thromboplastin time (PTT) test. The PTT is a test of the intrinsic (factors VIII, IX, XI, and XII) and common (fibrinogen, prothrombin, factors V and X) pathways of coagulation. A mixture of plasma and phospholipid platelet substitute (rabbit brain cephalin) is recalcified and the time required for the appearance of fibrin strands measured.

The PTT was tested to determine whether Compound I or Compound II have the ability to extend the control PTT. A test tube of rabbit brain cephalin (Sigma #RBC) in 0.85% NaCl and a test tube of 0.02 M $CaCl_2$ was brought to 37° C. in a water bath. Dade Ci-trol coagulation control lyophilized plasma (Dade International, Inc., product no. 34224–10) was reconstituted in sterile deionized water. In 10×75 mm glass test tubes, 100 µl reconstituted plasma and 100 µl RBC were mixed and incubated at 37° C. in a water bath for 5 minutes. Next, 50 µl of sample (deionized water, a photocrosslinkable polyvinylpyrrolidone (available from SurModics, Inc., product no. PVO5), or Compound I or II) was added and mixed. While simultaneously starting a stop watch, 100 µl of 0.02 M $CaCl_2$ was added to initiate the clotting cascade. After 40 seconds had passed, the test tubes were shaken lightly, observed for fibrin formation, and the number of seconds was recorded.

All samples were tested in duplicate. The appropriate control PTT, depending upon what solvent in which the reagent was dissolved, was subtracted from the average PTT for the reagent to give the time the control PTT was extended.

The results of a PTT experiment with two different concentrations of each reagent are shown in Table 1. The polymer PVO5, which does not have any sulfonate groups, did not extend the deionized water control PTT. Compounds I and II, which contain sulfonate groups, were able to considerably extend their control PTT's at both concentrations tested. At the higher of the two final concentrations tested, Compound II is able to extend the PTT from its water control by 1 hour or more, and Compound II is able to extend the 50% IPA control PTT by 1 hour. These results show that the reagents were able to inhibit the coagulation cascade, and therefore could be beneficial for hemocompatible applications.

TABLE 1

PTT of sulfonate reagents.

| Sample | Final Concentration (mg/ml) | Solvent | Formed Clot | Average PTT (seconds) | Time Extended Beyond Control PTT (seconds) |
|---|---|---|---|---|---|
| DI $H_2O$ control | — | — | yes | 53 | — |
| 50% IPA control | — | — | yes | 78 | — |
| PVO5 | 0.7 | $H_2O$ | yes | 53 | 0 |
| Compound I | 0.7 | $H_2O$ | yes | 117 | 64 |
| Compound II | 0.7 | 50% IPA | yes | 134 | 56 |
| Compound I | 1.43 | $H_2O$ | no | >3600 | >3600 |
| Compound II | 1.29 | 50% IPA | yes | 3600 | 3522 |

What is claimed is:

1. A reagent useful as a surface coating agent, the reagent comprising a nonpolymeric core molecule comprising an aromatic group, the core molecule having attached thereto, either directly or indirectly, one or more substituents comprising negatively charged groups, and two or more photoreactive species, wherein the reagent is selected from the group 4,5-bis(4-benzoylphenylmethyleneoxy)benzene-1,3-disulfonic acid di(potassium and/or sodium) salt, 2,5-bis(4-benzoylphenylmethyleneoxy)benzene-1,4-disulfonic acid di(potassium and/or sodium) salt, 2,5-bis(4-benzoylphenylmethyleneoxy)benzene-1-disulfonic acid monopotassium and/or monopotassium salt.

* * * * *